United States Patent [19]
Ebata et al.

[11] Patent Number: 5,786,887
[45] Date of Patent: Jul. 28, 1998

[54] ATOMIC ABSORPTION SPECTROPHOTOMETER AND ATOMIC ABSORPTION SPECTROCHEMICAL ANALYSIS

[75] Inventors: Yoshisada Ebata; Kazuo Moriya; Hisashi Kimoto, all of Hitachinaka; Hayato Tobe, Mito; Yasushi Terui, Hitachinaka, all of Japan

[73] Assignee: Hitachi, Ltd., Tokyo, Japan

[21] Appl. No.: 708,484

[22] Filed: Sep. 5, 1996

[30] Foreign Application Priority Data

Sep. 20, 1995 [JP] Japan ..................... 7-241375

[51] Int. Cl.$^6$ ....................................... B01N 21/00
[52] U.S. Cl. ..................... 356/73; 356/312; 356/315
[58] Field of Search ..................... 356/312, 311, 356/315, 316, 73; 250/214 AG

[56] References Cited

U.S. PATENT DOCUMENTS

| | | | |
|---|---|---|---|
| 3,610,760 | 10/1971 | Lowe. | |
| 3,824,016 | 7/1974 | Woodriff et al. | 356/312 |
| 4,061,925 | 12/1977 | Van der Gaag et al. | 250/214 AG X |
| 4,406,541 | 9/1983 | Tomoff et al. | 356/312 |
| 4,890,919 | 1/1990 | Tsukada et al. | |
| 5,181,077 | 1/1993 | Dencks et al. | 356/312 |
| 5,579,104 | 11/1996 | Honda et al. | 356/312 |

FOREIGN PATENT DOCUMENTS

| | | |
|---|---|---|
| 32 23 334 | 1/1984 | Germany. |
| 39 02 390 | 10/1989 | Germany. |
| 39 26 090 | 2/1991 | Germany. |
| 60-29893 | 7/1985 | Japan. |
| 2 066 501 | 7/1981 | United Kingdom. |

OTHER PUBLICATIONS

The Review of Scientific Instruments, 41, 1970, pp. 1168–1170, E. J. Rapperport et al.: *An Automated Atomic Absorption Spectrophotometer for the Acquisition of Termodynamic Data.*

Fresenius Z Anal. Chem (1987) 326–509, Springer Verlag, pp. 495–509, Broekaert et al.: *Recent developments in atomic spectrometry methods for elemental trace determinations.*

*Primary Examiner*—K. Hantis
*Attorney, Agent, or Firm*—Kenyon & Kenyon

[57] ABSTRACT

A light beam emitted by a hollow cathode lamp is concentrated on a central portion of an electrothermal sample atomizing apparatus by a concave mirror. The light concentrated on the central portion of the electrothermal sample atomizing apparatus is further concentrated on a central portion of a flame produced in a burner type sample atomizing apparatus by a lens. The light traveled through the burner type sample atomizing apparatus is condensed by a concave mirror, reflected by a flat mirror, and concentrated on an entrance slit of a spectroscope. Light outgoing through an exit slit of the spectroscope is detected by a photodetector.

6 Claims, 2 Drawing Sheets

ATOMIC ABSORPTION SPECTROPHOTOMETER AND ATOMIC ABSORPTION SPECTROCHEMICAL ANALYSIS

BACKGROUND OF THE INVENTION

The present invention relates to an atomic absorption spectrophotometer and an atomic absorption spectrochemical analysis and, more particularly, to an atomic absorption spectrophotometer and an atomic absorption spectrochemical analysis suitable for sensitive analysis.

A prior art atomic absorption photometer disclosed in, for example, JP-B No. 60-29893 has at least two types of sample atomizers placed in series on an optical path between a light source and a photodetector.

In this atomic absorption photometer, a burner type sample atomizing apparatus which introduces a mist of a sample into a flame and atomizes the sample is disposed near the light source, and an electrothermal type sample atomizing apparatus which introduces a sample into a cuvette made of graphite and heats the cuvette at a high temperature to atomize the sample is disposed between the burner type sample atomizing apparatus and a spectroscope. The atomic absorption photometer is used for the measurement of minor harmful elements in the fields of clinical medicine and environmental analysis owing to its capability of achieving the sensitive analysis of samples in an accuracy on the order of ppb (parts per billion). Recently, water quality standards have been amended. Whereas the former drinking water quality standards require drinking water not to contain any arsenic (As) and any selenium (Se) at all, the amended drinking water quality standards prescribe that water is drinkable when the As and Se concentration of the water is not higher than 10 ppb.

To achieve the quantitative analysis of elements having a concentration of 10 ppb or below, the relative standard deviation, i.e., (standard deviation)/(mean), of measurements obtained by repeated measurement of a standard sample having an As concentration and a Se concentration of 1 ppb must be 10% or below, and the limit of detection of an atomic absorption photometer must be as small as 0.3 ppb.

The ordinary atomic absorption photometer is incapable of detection with high accuracy of such a small limit of detection. Generally, the electrothermal type atomizing apparatus is capable of sensitive analysis in a sensitivity on the order of ppb. However, it is difficult to achieve a limit of detection of 0.3 ppb with the electrothermal type atomizing apparatus. A special analysis method uses a hydride generating apparatus attached to an atomic absorption photometer for generating arsenic hydride and selenium hydride, and a burner type atomizing apparatus using a heating quartz cell for determination. However, this analysis method needs much measuring time. The hydride generation apparatus needs five milliliters of sample for measurement. This necessary quantity of sample is about one hundred times the quantity of several microliters of sample required by the electrothermal type atomizing apparatus. Although such a large quantity of sample is not a problem when the sample is drinking water, such a large quantity of sample is not available when analyzing foods for As and Se, and hence the special analysis method is not practical or suitable for measurement.

SUMMARY OF THE INVENTION

It is an object of the present invention to solve the foregoing problems.

Another object of the present invention is to provide an atomic absorption photometer employing an electrothermal type sample atomizing apparatus and capable of achieving sensitive analysis at a sensitivity higher than that of the prior art atomic absorption photometer.

The present invention employs two types of sample atomizing apparatuses for atomic absorption photometric analysis. The sample atomizing apparatuses are disposed on an optical path and used selectively for analysis.

Preferably, in the atomic absorption spectrophotometer comprising two or more types of sample atomizing apparatuses disposed in a series arrangement on an optical path between a light source and a photodetector and used selectively for analysis, an electrothermal type sample atomizing apparatus is disposed near the light source, and a burner type sample atomizing apparatus is disposed between the electrothermal type sample atomizing apparatus and the photodetector.

Preferably, the atomic absorption spectrophotometer further comprises a lamp driving means for supplying a lamp driving current composed of a dc current and a low-frequency pulse current to the light source, and a low-frequency amplifying means for amplifying the low-frequency output signals of the photodetector. The low-frequency amplifying means operates for amplification in synchronism with the lamp driving current supplied by the lamp driving means to the light source.

Preferably, the atomic absorption spectrophotometer employs a concave mirror as an image forming element for concentrating light emitted by the light source on the central portion of the electrothermal type sample atomizing apparatus.

Preferably, the atomic absorption spectrophotometer further comprises a concave mirror as an image forming element for concentrating the light concentrated on the electrothermal type sample atomizing apparatus on the burner type sample atomizing apparatus.

According to the present invention, the electrothermal type sample atomizing apparatus is disposed near the light source, and the burner type sample atomizing apparatus is disposed between the electrothermal type sample atomizing apparatus and the photodetector to reduce the effect of white light emitted by the electrothermal type sample atomizing apparatus.

The atomic absorption spectrophotometer has the lamp driving means for supplying a lamp driving current produced by superposing a low-frequency pulse current on a dc current, and a low-frequency amplifying means for amplifying the low-frequency output signals of the photodetector. The low-frequency amplifying means amplifies the output signals of the photodetector in synchronism with the lamp driving current to further reduce the influence of the white light emitted by the electrothermal type sample atomizing apparatus.

Since the concave mirror is employed as an image forming element for concentrating the light emitted by the light source on the central portion of the electrothermal type sample atomizing apparatus, chromatic aberration will not occur even when the wavelength is changed; the light can always be concentrated on an optimum position in the electrothermal type sample atomizing apparatus and, consequently, the sensitivity can be improved.

Since the concave mirror is employed as an image forming element for concentrating the light emitted by the electrothermal type sample atomizing apparatus on the burner type sample atomizing apparatus, chromatic aberration will not occur even when the wavelength is changed; the light can always be concentrated on an optimum position in the burner type sample atomizing apparatus and, consequently, the sensitivity can be improved.

DETAILED DESCRIPTION

Figure 1:
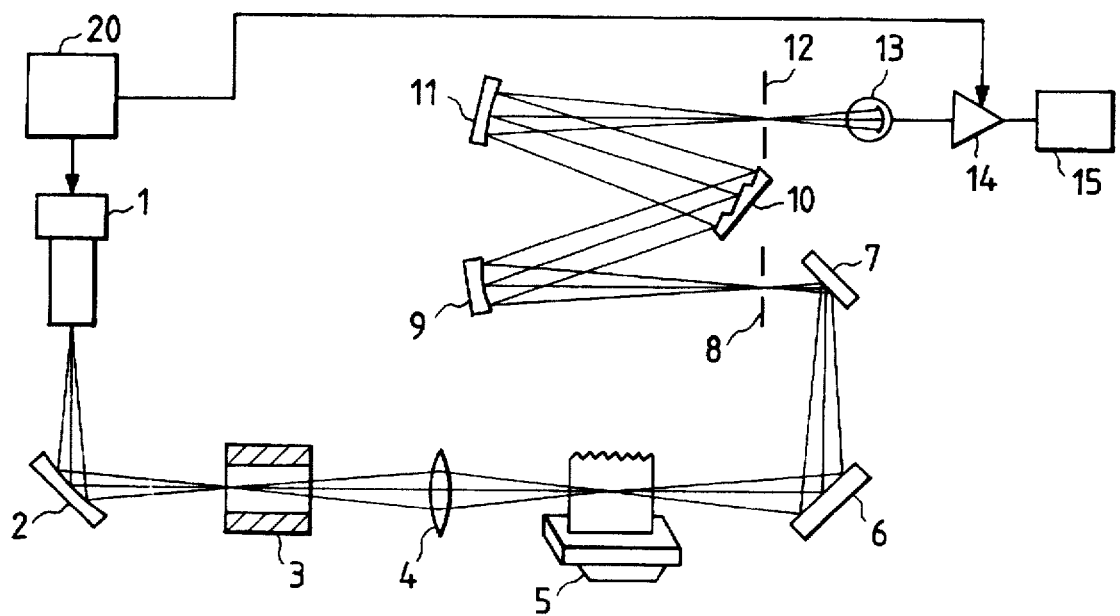
FIG. 1 is a diagrammatic view of an atomic absorption spectrophotometer in a first embodiment according to the present invention.

Referring to FIG. 1 showing an atomic absorption spectrophotometer in a first embodiment according to the present invention, a hollow cathode lamp 1, i.e., a light source, emits a light beam having atomic resonance lines of an emission spectrum of the same wavelengths as those of the absorption spectrum of atoms to be analyzed. A lamp driving device 20 supplies a lamp driving current produced by modulating a dc current by a pulse current of 100 Hz to the hollow cathode lamp 1. The hollow cathode lamp 1 is turned on and off in synchronism with the lamp driving current.

A light beam emitted by the hollow cathode lamp 1 is concentrated on a central portion of an electrothermal type sample atomizing apparatus 3 by a concave mirror 2. The electrothermal type sample atomizing apparatus 3 has a cylindrical graphite cuvette. The cuvette is heated at a high temperature by supplying an electric current thereto. The temperature of the cuvette is increased sequentially for drying, ashing and atomization to atomize a sample introduced into the cuvette.

The light beam concentrated on the central portion of the electrothermal type sample atomizing apparatus 3 is concentrated on a central portion of the flame produced in a burner type sample atomizing apparatus 5. The burner type sample atomizing apparatus 5 forms a flame of an inflammable gas, such as acetylene, and an atomized sample is introduced into the flame for thermal atomization. Since the lens 4 is employed as an image forming element, the position in the flame in the burner type sample atomizing apparatus 5 on which the light beam is concentrated is dependent on the wavelength due to chromatic aberration caused by the lens 4. However, since the length of the frame along the optical axis is about 100 mm, the influence of 10-odd mm dislocation of the position of image formation is not very significant. Since the sensitivity of the burner type sample atomizing apparatus 5 is low as compared with that of the electrothermal type sample atomizing apparatus 3 due to its atomizing efficiency and the stability of the flame, the influence of the use of a lens optical system is not very significant.

The light beam traveling through the burner type sample atomizing apparatus 5 is condensed by a concave mirror 6, reflected by a flat mirror 7 and concentrated on an entrance slit 8 of a spectroscope. The spectroscope comprises the entrance slit 8, a collimating mirror 9, a diffraction grating 10, a camera mirror 11 and an exit slit 12. The light beam traveling through the entrance slit 8 is collimated in a parallel beam by the collimating mirror 9 and is dispersed by the diffraction grating 10. The resonance absorption line of the same atom as the dispersed sample atoms is focused on the exit slit 12 by the camera mirror 11 and falls on a photodetector 13, such as a photomultiplier.

The output signal of the photodetector 13 is amplified by a dc amplifier 14. The dc amplifier 14 operates in synchronism with the operation of the lamp driving device 20. The dc amplifier 14 holds the output signal of the photodetector 13 while the lamp driving current supplied to the hollow cathode lamp 1 is not modulated by the pulse signal, and provides the difference between the output signal of the photodetector 13 while the lamp driving current is not modulated by the pulse signal and the output signal of the photodetector 13 while the lamp driving current is modulated by the pulse signal to reduce the influence of white light emitted by the electrothermal type sample atomizing apparatus 3. The dc amplifier 14 does not amplify high-frequency noise signals, but improves the S/N ratio and prevents the reduction of sensitivity due to the interference of noise signals with the faint signal. A data processor 15 processes the output signal of the dc amplifier 14 to display absorbance and to determine the density of the sample on the basis of a predetermined analytical curve.

The electrothermal type sample atomizing apparatus 3 is not used when the burner type sample atomizing apparatus 5 is used. The burner type sample atomizing apparatus 5 is not used when the electrothermal sample atomizing apparatus 3 is used.

In the conventional atomic absorption photometer, light emitted by the hollow cathode lamp is modulated by a modulating signal of 1800 Hz. Such modulation is achieved by supplying a current produced by superposing a 1800 Hz pulse current on a dc current. The hollow cathode lamp is driven for high-speed on-off operation by the modulated dc current, which is necessary to eliminate the influence of white light emitted by the cuvette of the electrothermal type sample atomizing apparatus because the electrothermal type sample atomizing apparatus is heated at about 3000° C.

An emission spectrum emitted by the hollow cathode lamp and the white light emitted by the cuvette fall simultaneously on the photomultiplier, i.e., a photodetector, and the emission spectrum and the white light are converted into corresponding electric signals. The light emitted by the hollow cathode lamp includes an ac component of 1800 Hz, while the white light emitted by the cuvette comprises dc components. Therefore, an ac amplifier is used for amplifying the output signal of the photodetector to eliminate the white light emitted by the cuvette.

However, since the output signal of the photomultiplier is of a low level, the noise component generated by the ac amplifier is amplified when the output signal of the photodetector is amplified by a plurality of stages of amplifiers.

When the concentration of the sample is high, the level of a signal to be amplified by the amplifier is sufficiently high as compared with that of the noise component and hence the noise component is not an obstacle to analysis. When the detection limit is as small as, for example, 0.3 ppb, the level of signals to be amplified by the amplifier is very low and the signals are buried in the noise components. Consequently, the conventional atomic absorption photometer is incapable of analyzing a small concentration of 0.3 ppb.

Such a problem may be solved by using a low-frequency or dc amplifier instead of the ac amplifier to process signals in a dc processing mode. However, the use of a low-frequency or dc amplifier makes the elimination of the influence of the white light emitted by the cuvette difficult. The influence of the white light on the measurement of arsenic (As) and selenium (Se) is particularly significant. The absorption spectrum of arsenic (As) is at 193 nm and that of selenium (Se) is at 196 nm. On the other hand, the emission spectrum of white light is dependent on color temperature. A peak of an emission spectrum is around 1400 nm when the color temperature is 2000° K. and light in the ultraviolet region corresponding to the absorption spectra of arsenic (As) and selenium (Se) is emitted scarcely. The quantity of light in an ultraviolet region beyond 190 nm increases when the color temperature is 3000° K. and the influence of the white light becomes significant.

Accordingly, in this embodiment, the electrothermal type sample atomizing apparatus 3 is disposed near the hollow cathode lamp 1, i.e., the light source, and the burner type sample atomizing apparatus 5 is disposed between the electrothermal type sample atomizing apparatus 3 and the spectroscope. The distance between the concave mirror 6 and the electrothermal type sample atomizing apparatus 3 is 470 mm, while the distance between the entrance slit of the spectroscope and the concave mirror 6 is about 220 mm and the distance between the concave mirror 6 and the electrothermal type sample atomizing apparatus is 170 mm in the conventional atomic absorption photometer. Since the distance is about three times the corresponding distance in the conventional atomic absorption photometer as viewed from the side of the entrance slit of the spectroscope, the influence of the white light emitted by the electrothermal type sample atomizing apparatus 3 in a contained angle at the entrance slit can be reduced to about ⅑.

The influence of the white light emitted by the electrothermal type sample atomizing apparatus 3 can be eliminated by intermittently turning on the hollow cathode lamp 1, i.e., a light source, at a low frequency of 100 Hz by means of an electric circuit, using a dc amplifier and amplifying signals in synchronism with the light source modulating frequency so that the dc components are removed.

The conventional atomic absorption photometer uses a lens for concentrating the light emitted by the light source on the burner type sample atomizing apparatus, i.e., a first sample atomizing apparatus, and a lens for concentrating the light on the electrothermal type sample atomizing apparatus, i.e., a second sample atomizing apparatus. Since the two lenses are disposed between the light source and the electrothermal type sample atomizing apparatus, the image formation position in the electrothermal type sample atomizing apparatus is dislocated due to chromatic aberration caused by the two lenses. The graphite cuvette of the electrothermal type sample atomizing apparatus has a cylindrical shape of about 30 mm in length. A sample is placed in the central portion of the inner space of the cuvette and heated at a high temperature for atomization, and a carrier gas is supplied through the opposite ends of the cuvette into the internal space to confine an atomic vapor in a central region of several millimeters for sensitive analysis. The atomic absorption photometer is designed so that an image of the light source is formed at the center of the cuvette of the electrothermal type sample atomizing apparatus when the light source emits light of 500 nm. When light of 190 nm is used for measurement as in the measurement of arsenic (As) and selenium (Se), the image forming position is dislocated about 15 mm from the center of the cuvette toward the side of the light source due to chromatic aberration caused by the lens. Consequently, the image of the light source is not formed at the center of the cuvette where the atomic vapor is the densest, so that the sensitivity of analysis is deteriorated.

Since the image forming optical system of this embodiment of the present invention employs the concave mirrors instead of the lenses, no problem attributable to chromatic aberration arises. Therefore, an image of the light source can be formed at the center of the cuvette of the electrothermal type sample atomizing apparatus where the density of the atomic vapor is the highest even if light of a wavelength in the ultraviolet region is used for measuring arsenic (As) and selenium (Se), so that sensitive analysis is possible.

When two lenses are used as in the conventional atomic absorption photometer, the position of an image of the light source is dislocated at the entrance slit of the spectroscope by chromatic aberration. If the position of the image is dislocated, the incident light is eclipsed by the entrance slit. Consequently, the quantity of light that falls on the photodetector decreases and the S/N ratio decreases. However, when the concave mirrors are employed as image forming elements as in this embodiment, the position of the image of the light source at the entrance slit of the spectroscope is not dislocated and the S/N ratio is improved.

In this embodiment, since the electrothermal type sample atomizing apparatus 3 that emits white light when measuring the sample is disposed remote from the spectroscope, the components of the white light that may reach the photodetector can be removed and a correct absorption signal can be obtained.

Since the light beam emitted by the hollow cathode lamp 1 is concentrated on the center of the electrothermal type sample atomizing apparatus 3 by the concave mirror 2 which does not cause chromatic aberration, the light beam can be concentrated on the predetermined position in the central portion of the cuvette and a correct absorption signal can be obtained regardless of the kind of the sample element when the electrothermal type sample atomizing apparatus 3 is used.

The light beam traveling through the electrothermal type sample atomizing apparatus 3 is subject to the influence of chromatic aberration because the light beam is concentrated by the lens 4. However, the effect of the lens 4 on the light beam is less significant than that of the two lenses of the conventional at omic absorption photometer. Since the light beam emitted by the hollow cathode lamp 1 reaches the photodetector 13 efficiently, measurement at a satisfactory S/N ratio can be achieved.

The electrothermal type sample atomizing apparatus 3 is disposed below the concave mirror 2 which does not cause chromatic aberration because the sectional area of a passage for the light beam of the electrothermal type sample atomizing apparatus 3 is smaller than that of the burner type sample atomizing apparatus 5, and the electrothermal type sample atomizing apparatus 3 is more susceptible to chromatic aberration than the burner type sample atomizing apparatus 5.

An atomic absorption spectrophotometer in a second embodiment according to the present invention will be described hereinafter with reference to FIG. 2.

Figure 2:
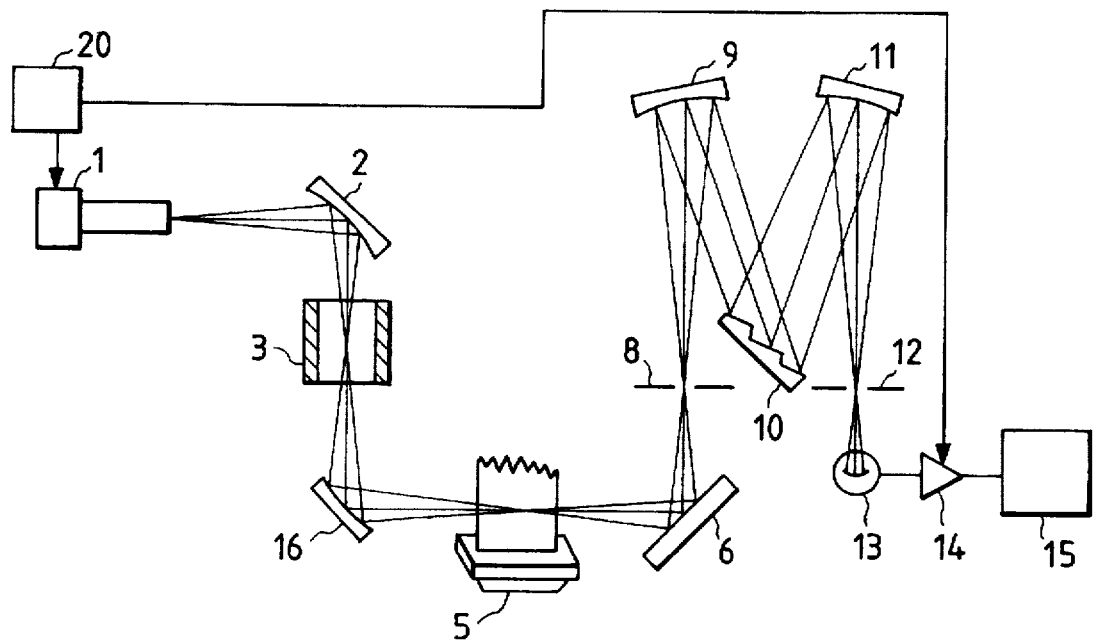
FIG. 2 is a diagrammatic view of an atomic absorption spectrophotometer in a second embodiment according to the present invention.

Referring to FIG. 2, a hollow cathode lamp 1, i.e., a light source, emits a light beam having atomic resonance lines of an emission spectrum of the same wavelengths as those of the absorption spectrum of atoms to be analyzed. A lamp driving device 20 supplies a lamp driving current produced by modulating a dc current by a pulse current of 100 Hz to the hollow cathode lamp 1. The hollow cathode lamp 1 is turned on and off in synchronism with the lamp driving current.

A light beam emitted by the hollow cathode lamp 1 is concentrated on a central portion of an electrothermal type sample atomizing apparatus 3 by a concave mirror 2. The electrothermal type sample atomizing apparatus 3 has a cylindrical graphite cuvette. The cuvette is heated at a high temperature by supplying an electric current thereto. The temperature of the cuvette is increased sequentially for drying, ashing and atomization to atomize a sample introduced into the cuvette.

The light beam concentrated on the central portion of the electrothermal type sample atomizing apparatus 3 is concentrated on a central portion of the flame produced in a burner type sample atomizing apparatus 5. The burner type sample atomizing apparatus 5 forms a flame of an inflammable gas, such as acetylene, and an atomized sample is introduced into the flame for thermal atomization.

The light beam traveling through the burner type sample atomizing apparatus 5 is condensed by a concave mirror 6, and concentrated on an entrance slit 8 of a spectroscope. The spectroscope comprises the entrance slit 8, a collimating mirror 9, a diffraction grating 10, a camera mirror 11 and an exit slit 12. The light beam traveling through the entrance slit 8 is collimated in a parallel beam by the collimating mirror 9 and is dispersed by the diffraction grating 10. The resonance absorption line of the same atom as the dispersed sample atoms is focused on the exit slit 12 by the camera mirror 11 and falls on a photodetector 13, such as a photomultiplier.

The output signal of the photodetector 13 is amplified by a dc amplifier 14. The dc amplifier 14 operates in synchronism with the operation of the lamp driving device 20. The dc amplifier 14 holds the output signal of the photodetector 13 while the lamp driving current supplied to the hollow cathode lamp 1 is not modulated by the pulse signal, and provides the difference between the output signal of the photodetector 13 while the lamp driving current is not modulated by the pulse signal and the output signal of the photodetector 13 while the lamp driving current is modulated by the pulse signal to reduce the influence of white light emitted by the electrothermal type sample atomizing apparatus 3. The dc amplifier 14 does not amplify high-frequency noise signals, but improves the S/N ratio and prevents the reduction of sensitivity due to the interference of noise signals with the faint signal. A data processor 15 processes the output signal of the dc amplifier 14 to display absorbance and to determine the density of the sample on the basis of a predetermined analytical curve.

The electrothermal type sample atomizing apparatus 3 is not used when the burner type sample atomizing apparatus 5 is used. The burner type sample atomizing apparatus 5 is not used when the electrothermal sample atomizing apparatus 3 is used.

In this embodiment, since the electrothermal type sample atomizing apparatus 3 that emits white light when measuring the sample is disposed remote from the spectroscope, the components of the white light that may reach the photodetector can be removed and a correct absorption signal can be obtained.

Since the light beam emitted by the hollow cathode lamp 1 is concentrated on the center of the electrothermal type sample atomizing apparatus 3 by a first concave mirror 2 which does not cause chromatic aberration, and on the center of a flame in the burner type sample atomizing apparatus 5 by a second concave mirror 16 which does not cause chromatic aberration, the light beam can always be concentrated on the predetermined position during measurement either when the electrothermal type sample atomizing apparatus 3 is used or when the burner type sample atomizing apparatus 5 is used regardless of the elements to be measured, so that correct signals can always be obtained.

Since the atomic absorption spectrophotometer does not employ any lenses which cause chromatic aberration, the light beam emitted by the hollow cathode lamp 1 is always concentrated on the entrance slit 8 of the spectroscope and hence measurement can be achieved at a satisfactory S/N ratio.

An atomic absorption spectrophotometer in a third embodiment according to the present invention will be described with reference to FIG. 3.

Figure 3:
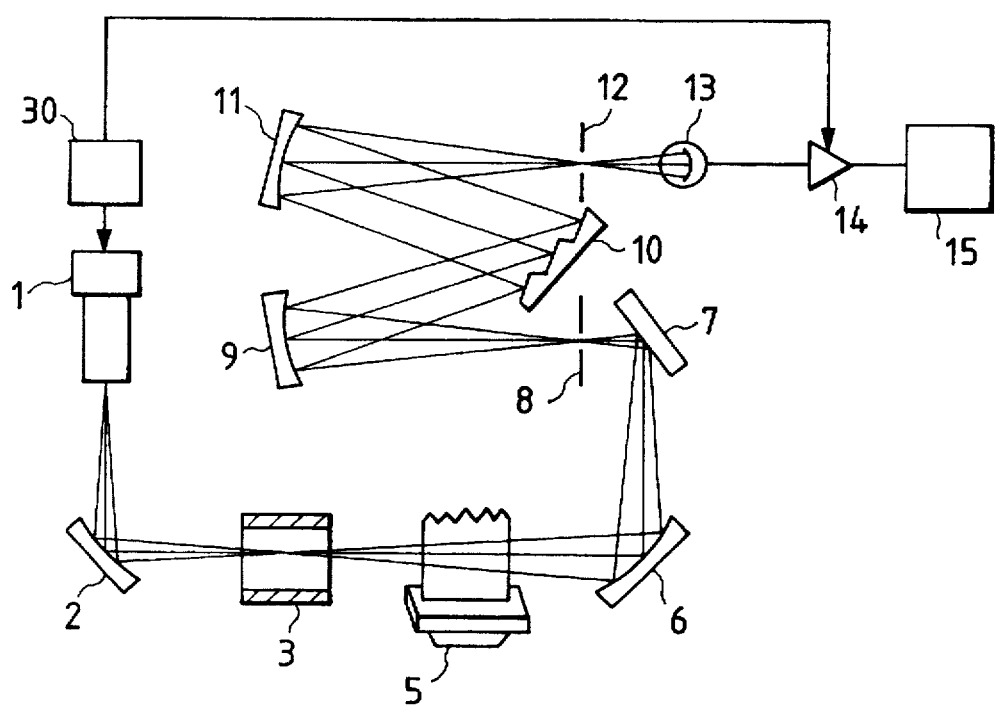
FIG. 3 is a diagrammatic view of an atomic absorption spectrophotometer in a third embodiment according to the present invention.

Referring to FIG. 3, a hollow cathode lamp 1, i.e., a light source, emits a light beam having atomic resonance lines of an emission spectrum of the same wavelengths as those of the absorption spectrum of atoms to be analyzed. A lamp driving device 30 supplies a lamp driving current produced by modulating a dc current by a pulse current of 100 Hz to the hollow cathode lamp 1. The hollow cathode lamp 1 is turned on and off in synchronism with the lamp driving current.

A light beam emitted by the hollow cathode lamp 1 is concentrated on a central portion of an electrothermal type sample atomizing apparatus 3 by a concave mirror 2. The electrothermal type sample atomizing apparatus 3 has a cylindrical graphite cuvette. The cuvette is heated at a high temperature by supplying an electric current thereto. The temperature of the cuvette is increased sequentially for drying, ashing and atomization to atomize a sample introduced into the cuvette.

The light beam concentrated on the central portion of the electrothermal type sample atomizing apparatus 3 is concentrated on a central portion of the flame produced in a burner type sample atomizing apparatus 5. The burner type sample atomizing apparatus 5 forms a flame of an inflammable gas, such as acetylene, and an atomized sample is introduced into the flame for thermal atomization.

The light beam traveling through the burner type sample atomizing apparatus 5 is condensed by a concave mirror 6, reflected by a flat mirror 7 and concentrated on an entrance slit 8 of a spectroscope. The spectroscope comprises the entrance slit 8, a collimating mirror 9, a diffraction grating 10, a camera mirror 11 and an exit slit 12. The light beam traveling through the entrance slit 8 is collimated in a parallel beam by the collimating mirror 9 and is dispersed by the diffraction grating 10. The resonance absorption line of the same atom as the dispersed sample atoms is focused on the exit slit 12 by the camera mirror 11 and falls on a photodetector 13, such as a photomultiplier.

The output signal of the photodetector 13 is amplified by a dc amplifier 14. The dc amplifier 14 operates in synchronism with the operation of the lamp driving device 30. The dc amplifier 14 holds the output signal of the photodetector 13 while the lamp driving current supplied to the hollow cathode lamp 1 is not modulated by the pulse signal, and provides the difference between the output signal of the photodetector 13 while the lamp driving current is not modulated by the pulse signal and the output signal of the photodetector 13 while the lamp driving current is modulated by the pulse signal to reduce the influence of white light emitted by the electrothermal type sample atomizing apparatus 3. The dc amplifier 14 does not amplify high-frequency noise signals, but improves the S/N ratio and prevents the reduction of sensitivity due to the interference of noise signals with the faint signal. A data processor 15 processes the output signal of the dc amplifier 14 to display absorbance and to determine the density of the sample on the basis of a predetermined analytical curve.

The electrothermal type sample atomizing apparatus 3 is not used when the burner type sample atomizing apparatus 5 is used. The burner type sample at omizing apparatus 5 is not used when the electrothermal sample atomizing apparatus 3 is used.

In this embodiment, since the electrothermal type sample atomizing apparatus 3 that emits white light when measuring the sample is disposed remote from the spectroscope, the components of the white light that may reach the photodetector can be removed and a correct absorption signal can be obtained.

Since the light beam emitted by the hollow cathode lamp 1 is concentrated on the center of the electrothermal type sample atomizing apparatus 3 by a concave mirror 2 which does not cause chromatic aberration so that the light beam travels through the central portion of the flame formed in the burner type sample atomizing apparatus 5, the light beam can always be concentrated on the predetermined position during measurement either when the electrothermal type sample atomizing apparatus 3 is used or when the burner type sample atomizing apparatus 5 is used regardless of the elements to be measured, so that correct signals can always be obtained.

Since the atomic absorption spectrophotometer does not employ any lenses which cause chromatic aberration, the light beam emitted by the hollow cathode lamp 1 is always concentrated on the entrance slit 8 of the spectroscope and hence measurement can be achieved at a satisfactory S/N ratio.

Since only one concave mirror is used, the optical system of the atomic absorption spectrophotometer is simple. Although no image is formed in the burner type sample atomizing apparatus 5, analysis of low sensitivity on the order of ppb is possible because the length of the flame is about 100 mm. Since the electrothermal type sample atomizing apparatus and the burner type sample atomizing apparatus in this embodiment can be disposed close to each other, this embodiment is applicable to an atomic absorption spectrophotometer having an electrothermal sample atomizing apparatus and a burner type sample atomizing apparatus not provided with a magnet for background correction using the Zeeman effect. Thus, the atomic absorption spectrophotometer is capable of sensitive analysis.

What is claimed is:

1. An atomic absorption spectrophotometer comprising a light source emitting a beam of light; a photodetector; and two or more types of sample atomizing apparatus disposed in a series arrangement on an optical path between the light source and the photodetector and capable of being used selectively for analysis; the two or more types of sample atomizing apparatus including an electrothermal type sample atomizing apparatus and a burner type sample atomizing apparatus, the electrothermal type sample atomizing apparatus and the burner type sample atomizing apparatus being disposed so that the burner type sample atomizing apparatus is between the electrothermal type sample atomizing apparatus and the photodetector; a concave mirror between said light source and said electrothermal type sample atomizing apparatus acting as an image forming element for concentrating said light beam emitted by the light source on a central portion of the electrothermal type sample atomizing apparatus; and a lens disposed between said electrothermal type sample atomizing apparatus and said burner type sample atomizing apparatus, concentrating the light beam, after passing through said electrothermal type sample atomizing apparatus, on said burner type sample atomizing apparatus.

2. The atomic absorption spectrophotometer according to claim 1 further comprising: a lamp driving means for supplying a lamp driving current, obtained by superposing a low-frequency pulse current and a dc current, to the light source, and a low-frequency amplifying means for amplifying low-frequency output signals of the photodetector, the low-frequency amplifying means operating, for amplification, in synchronism with the lamp driving current supplied by the lamp driving means to the light source.

3. The atomic absorption spectrophotometer according to claim 1 wherein the electrothermal type sample atomizing apparatus is closer to the light source than the burner type sample atomizing apparatus.

4. An atomic absorption spectrochemical analysis using an atomic absorption spectrophotometer comprising two or more types of sample atomizing apparatus disposed in a series arrangement on an optical path between the light source and the photodetector; wherein an electrothermal type sample atomizing apparatus is disposed on the side of the light source, a burner type sample atomizing apparatus is disposed between the electrothermal type sample atomizing apparatus and the photodetector, and the two or more types of sample atomizing apparatus are used selectively; a concave mirror between said light source and said electrothermal type sample atomizing apparatus acting as an image forming element for concentrating said light beam emitted by the light source on a central portion of the electrothermal type sample atomizing apparatus; and a lens disposed between said electrothermal type sample atomizing apparatus and said burner type sample atomizing apparatus, concentrating the light beam, after passing through said electrothermal type sample atomizing apparatus, on said burner type sample atomizing apparatus.

5. The atomic absorption spectrochemical analysis according to claim 4, wherein a lamp driving current, obtained by superposing a low-frequency pulse current and a dc current, is supplied to the light source, and low-frequency output signals of the photodetector are amplified in synchronism with the lamp driving current supplied to the light source.

6. The atomic absorption spectrophotometer analysis according to claim 4 wherein the electrothermal type sample atomizing apparatus is closer to the light source than the burner type sample atomizing apparatus.

* * * * *